United States Patent
Fein et al.

(10) Patent No.: US 6,600,940 B1
(45) Date of Patent: Jul. 29, 2003

(54) OXIMETER SENSOR WITH DIGITAL MEMORY

(75) Inventors: Michael E. Fein, deceased, late of Mountain View, CA (US), by Marcia Fein, executrix; Paul D. Mannheimer, Danville, CA (US); Adnan Merchant, Fremont, CA (US); Bruce Bowman, Eden Prairie, MN (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/943,898

(22) Filed: Aug. 30, 2001

Related U.S. Application Data

(60) Provisional application No. 60/229,616, filed on Aug. 31, 2000.

(51) Int. Cl.[7] .................................. A61B 5/00
(52) U.S. Cl. ..................... 600/323; 600/331; 600/330
(58) Field of Search ............... 600/309–310, 600/322–323, 331, 330

(56) References Cited

U.S. PATENT DOCUMENTS

| 4,714,080 A | 12/1987 | Edgar, Jr. et al. |
| 4,862,872 A | 9/1989 | Yabe et al. |
| 4,913,150 A | 4/1990 | Cheung et al. |
| 5,007,423 A | 4/1991 | Branstetter et al. |
| 5,058,588 A * | 10/1991 | Kaestle ............... 600/323 |
| 5,425,375 A | 6/1995 | Chin et al. |
| 5,443,801 A | 8/1995 | Langford |
| 5,660,163 A | 8/1997 | Schulman et al. |
| 5,758,644 A * | 6/1998 | Diab et al. ............ 600/323 |
| 5,800,350 A | 9/1998 | Coppleson et al. |
| 5,830,121 A | 11/1998 | Enomoto et al. |
| 5,855,609 A | 1/1999 | Knapp |
| 5,987,343 A * | 11/1999 | Kinast ................. 600/323 |
| 6,044,283 A | 3/2000 | Fein et al. |
| 6,104,938 A | 8/2000 | Huiku et al. |
| 6,122,536 A | 9/2000 | Sun et al. |
| 6,241,679 B1 | 6/2001 | Curran |
| 6,298,255 B1 | 10/2001 | Cordero et al. |
| 6,308,089 B1 | 10/2001 | von der Ruhr et al. |
| 6,356,774 B1 | 3/2002 | Bernstein et al. |
| 6,360,114 B1 * | 3/2002 | Diab et al. ........... 600/336 |
| 6,377,829 B1 | 4/2002 | Al-Ali |
| 6,405,087 B1 | 6/2002 | Snell |
| 6,463,310 B1 | 10/2002 | Swedlow et al. |
| 6,466,808 B1 | 10/2002 | Chin et al. |

FOREIGN PATENT DOCUMENTS

| WO | WO97/29678 | 8/1997 |

* cited by examiner

Primary Examiner—Max F. Hindenburg
Assistant Examiner—Matthew Kremer
(74) Attorney, Agent, or Firm—Townsend and Townsend and Crew LLP; Steven J. Cahill

(57) ABSTRACT

The present invention provides a memory chip for use in an oximeter sensor, or an associated adapter or connector circuit. The memory chip allows the storing of different data to provide enhanced capabilities for the oximeter sensor. In addition to providing unique data to store in such a memory, the present invention describes unique uses of data stored in such a memory. The data stored in the memory chip includes data that can be used by an oximeter to determine if the sensor is adequately attached to the patient, data that indicates sensor assembly characteristics that can be used to correct for variations in optical efficiency, data that can provide compensation for infrared wavelength shifts caused by optical fiber, data relating to additional LEDs in the sensor, data indicating the last time the sensor was moved or disconnected, and data indicating whether the sensor is isolated.

9 Claims, 2 Drawing Sheets

OXIMETER SENSOR WITH DIGITAL MEMORY

CROSS-REFERENCES TO RELATED APPLICATIONS

This application claims priority to U.S. Provisional Patent Application No. 60/229,616, filed Aug. 31, 2000, which is hereby incorporated by reference herein.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood-perfused tissue, with a detector picking up light which has not been absorbed by the tmssue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength fov that temperature.

Another method of storing coded information regarding the characteristics of the LEDs is shown in U.S. Pat. No. 4,942,877 assigned to Minolta. This patent discloses using an EPROM memory to store digital information, wn, which can be provided in parallel or serially from the sensor probe to the remote oximeter. The memory is described as storing coefficients for the saturation equation, wavelength, sub- wavelength (where 2 peaks for LED), half-width of wavelength spectrum emitted by LED, intensity of LEDS or ratio, and on time of LEDS (written by the processor).

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register.

Typically, the coding element is mounted in the probe itself. For instance, U.S. Pat. No. 4,621,643 shows the coding resistor mounted in the probe element itself. In addition, U.S. Pat. No. 5,246,003 shows the coding resistor being formed wmth a printed conductive material on the probe itself.

In some devices, an electrical connector coupled by a cable to a device attached to a patient may include a coding elementor example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

Hewlett-Packard Company U.S. Pat. No. 5,058,588 teaches an oximeter sensor with an encoding element that could be resistor, ROM, or customized integrated circuit. The encoding element encodes the type of sensor (in particular, type indicating area of placement on body—finger, ear, foot, arm; also, the type of sensor can mndicate transmission/reflection type, or adult/neonate {indicating correction to be performed on theoretical oxygen saturation, allow switching between physiological limits such as minimum/maximum pulse rates for adults/neonates}; the maximum driving current may be adapted according to type of sensor, and contact of sensor with tissue can be tested by means of an attenuation measurement if sensor type is known).

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

A number of catheter patents also discuss encoding information in the catheter. Sentron U.S. Pat. No. 4,858,615 teaches encoding the type of sensor, type number, serial number, date of production, safe use life of the sensor, correction data for non-linearity, pressure sensitivity, offset, and temperature sensitivity.

Interflo Medical Published PCT Application No. PCT/US92/08263, Publication No. WO 93/06776 teaches encoding patient specific data, size, manufacture date, batch number, sterilization date, expiration date, transducer number and type, manufacturer's name and address, thermistor heating element resistance, filament efficiency, program segments or patient historical data., format version for the calibration data, trademark information, catheter unique serial number, ship date, other date and time information, security code to identify manufacturer, thermal mass, filament composition, coefficient of resistance, layout byte, checksum, copyright, number of seconds since a certain date, patient weight, patient height, timestamp of 1 st CO data point, and a count of all CO data points in EEPROM.

Dulex-Ohmeda of Boulder, Colo. markets an oximeter sensor product that encodes data into resistor values representing pointers to a lookup table containing coefficients (as in U.S. Pat. No. 4,700,708) as well as indicating a range of LED drive current to use with the sensor. The LEDs are driven with a higher or lower drive currents depending upon the value of the resistor in a particular sensor.

Honeywell U.S. Pat. No. 4,303,984 (expires Dec. 14, 1999) describes a memory which stores characterization information, such as linearization information for a pressure sensor. Alnor Instrument U.S. Pat. No. 5,162,725 describes storing both calibration and ID information in a sensor memory. Seimans U.S. Pat. No. 5,016,198 describes a coding memory in a sensor with data for defining sensor's characteristic curve. McBean U.S. Pat. No. 5,365,462 describes a date code in a sensor memory. Honeywell U.S. Pat. No. 4,734,873 describes a pressure sensor with a PROM storing coefficients for a polynomial. Robert Bosch U.S. Pat. No. 4,845,649 describes a PROM in a sensor storing correcting data.

McBean U.S. Pat. No. 5,371,128 relates to EEPROM in sensor with sensor type code and calibration data. McBean U.S. Pat. No. 5,347,476 an accuracy code. Otax U.S. Pat. No. 5,528,519 shows a PROM in a connector for oximeter.

Square D Company U.S. Pat. No. 5,070,732 shows calibration data in a sensor memory. Baxter U.S. Pat. No. 5,720,293 talks about different calibration information for a catheter, including a security code (encryption is discussed), serial number, model number, ID data such as calibration, manufacture, sterilization and ship date or other date and time information, a software program segment, security code for identifying whether sensor made by same manufacturer as monitor manufacturer, filament or transducer resistance, heat transfer coefficient, thermal mass, filament composition and coefficient of resistance, layout byte, copyright notice, checksum, random data bytes. Porsche U.S. Pat. No. 5,008,843 describes a sensor with EEPROM ID and characteristics data.

BRIEF SUMMARY OF THE INVENTION

The present invention provides a memory chip for use in an oximeter sensor, or an associated adapter or connector circuit. The memory chip allows the storing of different data to provide enhanced capabilities for the oximeter sensor. In addition to providing unique data to store in such a memory, the present invention describes unique uses of data stored in such a memory. The data stored in the memory chip includes data that can be used by an oximeter to determine if the sensor is adequately attached to the patient, data that indicates sensor assembly characteristics that can be used to correct for variations in optical efficiency, data that can provide compensation for infrared wavelength shifts caused by optical fiber, data relating to additional LEDs in the sensor, data indicating the last time the sensor was moved or disconnected, and data indicating whether the sensor is isolated.

DETAILED DESCRIPTION OF THE INVENTION

Figure 1:
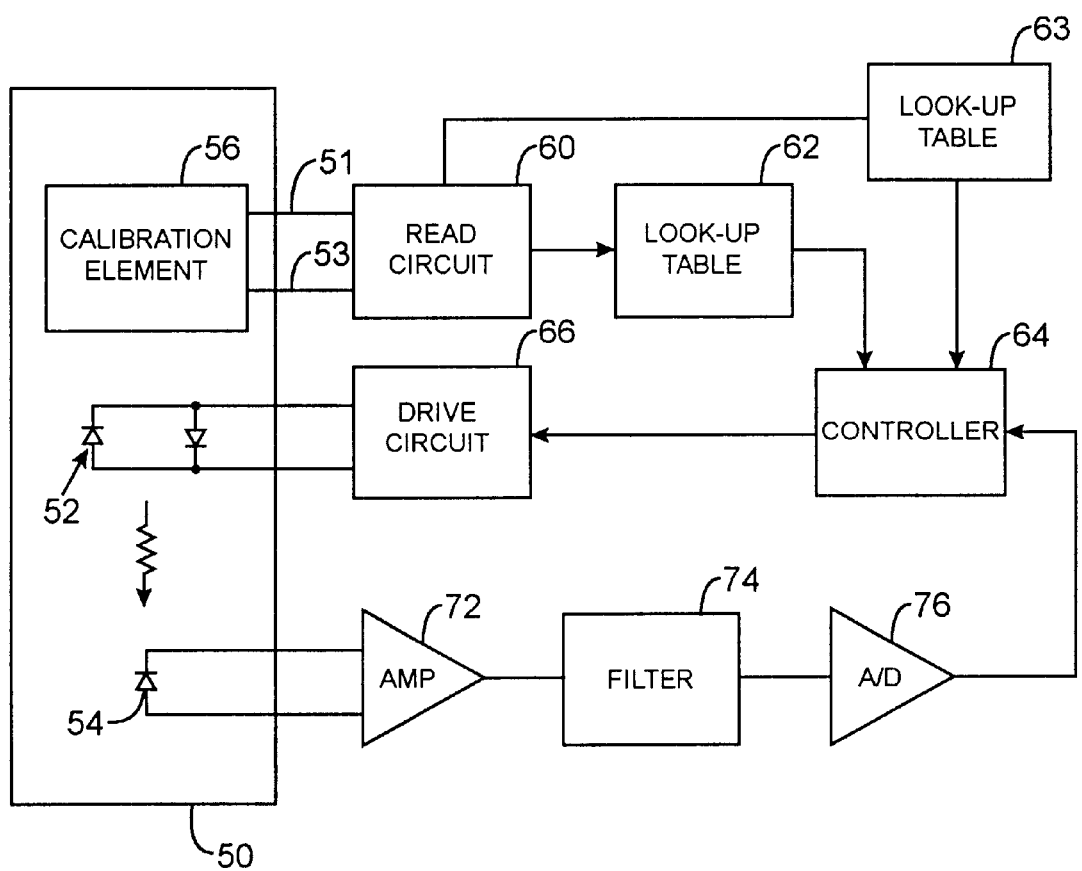
FIG. 1 is a block diagram of a pulse oximeter system in accordance with the present invention.

FIG. 1 is a block diagram of a pulse oximeter system incorporating a calibration memory element 56 according to the invention. In one embodiment, memory element 56 is a two-lead semiconductor digital memory chip. The calibration element is part of the sensor 50 which also includes red and infrared LEDs 52 as in the prior art, along with a detector 54. If desired, LEDs 52 may be replaced with other light emitting elements such as lasers.

The oximeter includes read circuit 60, drive circuit 66, look-up tables 62 and 63, controller 64, amplifier 72, filter 74, and analog-to-digital converter 76. Read circuit 60 is provided for reading multiple coded values across the two leads 51, 53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system. Controller 64 provides signals to a drive circuit 66, to control the amount of drive current provided to LEDs 52.

As in the prior art, detector 54 is connected through an amplifier 72 and a filter 74 to an A/D converter 76. This forms a feedback path used by controller 64 to adjust the drive current to optimize the intensity range of the signal received. For proper operation the signal must be within the analog range of the circuits employed. The signal should also be well within the range of A/D converter 76 (e.g., one rule that may be applied is to adjust LED drives and amplifier gains so that both red and IR signals fall between 40% and 80% of full scale reading of converter 76). This requires correct and independent settings for both the red and infrared LEDs. The current invention allows for another feedback path which may alter the LED settings based on other sensor characteristics contained in the coding of the calibration element 56, which is discussed in further detail below.

Memory 56 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations. Various types of data useful to a pulse oximetry system can be stored in memory 56 as will now be discussed.

In a first embodiment of the present invention, an extrinsic probe of skin contact can be used to indicate whether the sensor is in adequate contact to the patient. This extrinsic probe can include, for example, an impedance measurement across two electrodes. The electrodes can be similar to the contact electrodes of the Nellcor FS-14 fetal sensor. The two electrodes are exposed externally on the side of the sensor that contacts the skin of the patient. The two electrodes are coupled through wire connections to the oximeter monitor. The oximeter monitor applies a small voltage potential across the electrodes causing a small current to flow between the electrodes. If the sensor is adequately attached to the patient, a current flows through the patient's skin between the electrodes. If the sensor is not adequately attached to the patient, a medium conducive to current flow does not exist between the electrodes. The oximeter monitor measures the resulting current flow between the electrodes and calculates the impedance between the electrodes. The measured impedance is much larger when the sensor is not properly attached to a patient, because ambient air has a much higher resistance than skin.

A range for the impedance between the electrodes that is expected when the sensor is attached to a patient (or when the sensor is not attached to a patient) can be encoded into memory 56. The oximeter monitor can determine if the sensor is attached to a patient by determining if the measured impedance between the electrodes falls within the expected range encoded in memory 56. For example, the measured impedance falling within the expected range encoded in memory 56 can be indicative that the sensor is attached to the patient securely enough to obtain adequate signals from photodetector 54 that are indicative of patient blood oxygen saturation levels. If the measured impedance falls outside the expected range, the oximeter monitor can sound an alarm signal, and/or record a time stamp in memory 56 when the measured impedance indicates the sensor is not adequately attached to the patient. Dedicated sensor connector pins can be used for the electrodes, or, if desired, pin-sharing can be used for electrodes to accomplish the measure of sensor-patient contact.

In a further embodiment of the present invention, a force or pressure switch that is sensitive to whether adequate force or pressure is present in the sensor placement can be used to indicate whether the sensor is in adequate contact to the patient. The force or pressure switch may be, for example, a MEMS device, a fluidic switch, or other switches well-known to those of skill in the art. The force/pressure switch can be placed on the outside of the sensor on the side that contacts the patient. The switch is coupled to the oximeter monitor through connection wires. The oximeter monitor compares the pressure signal received from the pressure switch with an expected pressure range encoded in memory 56 to determine if the sensor is adequately attached to the patient. The pressure range encoded into memory 56 can be indicative of a pressure range expected when the sensor is attached or not attached to a patient. Other means for determining sensor-to-patient contact may be also be used, while encoding expected ranges in memory 56, in accordance with the present invention.

For physiological monitoring instruments that include a monitor and a patient sensor, the monitor may be unable to accurately determine a quality of a signal obtained from the sensor. The accuracy of the estimates of the blood flow characteristics depends on a number of factors. For example, the light absorption characteristics typically vary from patient to patient depending on their physiology. Moreover, the absorption characteristics vary depending on the location (e.g., the foot, finger, ear, and so on) where the sensor is applied. Further, the light absorption characteristics vary depending on the design or model of the sensor. Also, the light absorption characteristics of any single sensor design vary from sensor to sensor (e.g., due to different character- istics of the light sources or photo-detector, or both). The clinician applying the sensor correctly or incorrectly may also have a large impact in the results, for example, by loosely or firmly applying the sensor or by applying the sensor to a body part which is inappropriate for the particular sensor design being used.

Details of a Method and Circuit for Indicating Quality and Accuracy of Physiological Measurements are discussed in U.S. patent application Ser. No. 09/545,170, filed Apr. 6, 2000 to Porges, et al., which is incorporated by reference herein in its entirety. The invention discussed in the Porges et al. patent application provides a method and system for more accurately determining a quality of a signal detected by a sensor; a way of determining a relative accuracy of a physiological characteristic derived or calculated from the signal; and a way of delineating a transition boundary between a normal signal for the sensor being used in its normal application, and a signal considered to be abnormal for the sensor being used, to allow a monitor to determine if the sensor is being misapplied. The quality of a signal detected by an oximeter sensor and a relative accuracy of a physiological characteristic derived or calculated from the signal can be determined based upon the light level (or DC component) of the signal detected by the photodetector and the signal's modulation percentage, as discussed in further detail in U.S. patent application Ser. No. 09/545,170.

Signal data from the sensor that falls within a predetermined range of quality and accuracy levels for particular physiological characteristics (such as blood oxygen saturation) is referred to as a comparative oximetry performance (COP) space. Parameters that are relevant to determining where a patient's measured physiological characteristics lie in comparative oximetry performance space may be encoded into memory 56 of the sensor.

The inherent brightness of LEDs, the sensitivity of detector, and anything else about the particular sensor assembly (e.g. bandage color and alignment) can affect the amount of light which the sensor's photodetector receives. Variations in these parameters from sensor-to-sensor can significantly effect the ability of an oximeter monitor to determine if a patient's physiological parameters are within the COP space. In an embodiment of the present invention, parameters that are specific to a particular sensor or class of sensors (such as brightness of the LEDs, sensitivity of the photodetector, and other sensor assembly characteristics) can be encoded into memory 56 of the sensor. The oximeter monitor reads these sensor parameters from memory 56, and uses them to improve the oximeter's ability to determine the relative accuracy of blood oxygen saturation levels and other measured physiological parameters. Sensor parameters can be encoded into memory 56 by the manufacturer or calculated by the oximeter monitor.

The oximeter can use sensor parameters such as brightness of the LEDs and sensitivity of the photodetector that are encoded in memory 56 to compute a patient's optical transmissivity for each LED wavelength. A patient's optical transmissivity can also be used to improve the oximeter's ability to determine the relative accuracy of a patient's measured physiological characteristics. A patient's optical transmissivity depends almost entirely on the properties of the particular patient.

Signal to noise ratio of the oximeter is determined by the size of the detected signal, not by the transmissivity of the patient alone. The DC transmissivity of the patient's tissue can be used to improve the accuracy of pulse oximetry. The size of the signal received by photodetector 54 can be increased by driving LEDs 52 with a greater drive current in patients that have a lower transmissivity to improve the signal to noise ratio of the detected signal.

In another embodiment of the present invention, LED and detector parameters are recorded in sensor memory 56 to provide a basis for later research on drift of these parameters due to various environmental conditions which the sensor experiences. For example, the oximeter monitor can keep track of changes in the signal from photodetector 54 to determine variations in the LED and detector parameters over time and record these changes in memory 56. Parameters of interest include not only LED power and detector sensitivity but also LED wavelengths, spectral width (full width at half maximum), and secondary emission level.

The relative wavelengths of the red and infrared (IR) light that are used to make the measurement in oximetry are very important to know so that calibration can be maintained. In traditional LED oximetry, the LED sources are at the skin so that whatever wavelength is emitted is what is sensed by the photodiode that receives the light. The red LED is the primary one that needs to be characterized for accurate saturation measurements to be realized. The saturation is less sensitive to the IR wavelength provided it remains with an acceptable range.

In some oximeter sensors, plastic optical fibers are used for the transmission of light. When using plastic fibers for transmission of the light, there is a wavelength dependent absorption caused by the fiber. This has the effect of altering the apparent center wavelength of one or both of the read and IR sources, which can affect calibration of the unit. By characterizing the fiber for its shift or shifts, the proper compensation in the algorithm used by the oximeter to calculate the blood oxygen saturation can be stored in memory 56. The compensation may be correction factors or the actual coefficients used for calculating blood oxygen saturation. The oximeter can read the compensation data in memory 56 and use this data to restore the accuracy that would otherwise be lost in fiber transmission of the light.

Figure 2:
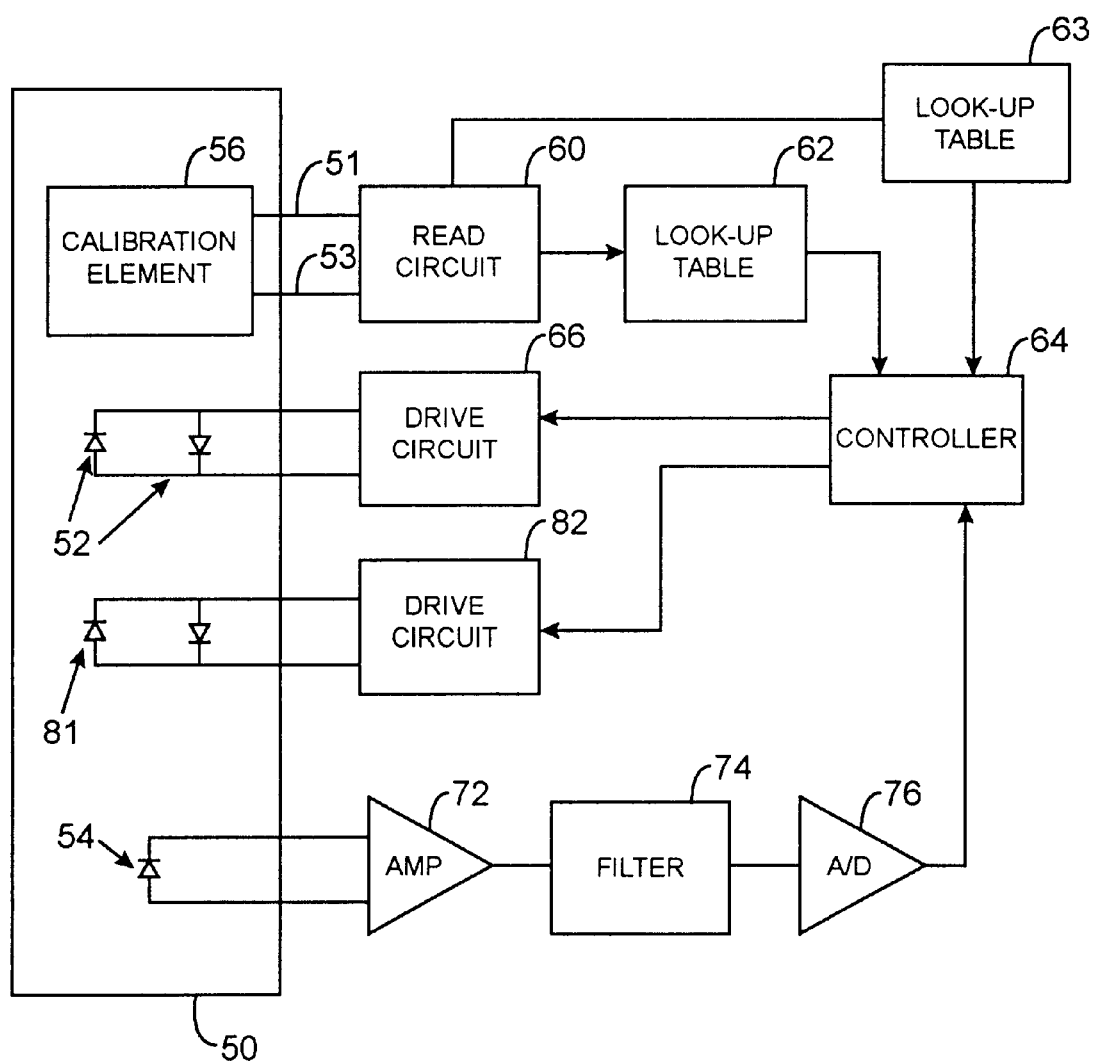
FIG. 2 is a block diagram of a second embodiment of a pulse oximeter system in accordance with the present invention.

There are limitations on the number and type of blood constituents that can be sensed using the two conventional LED 52 wavelengths of the oximeter. The accuracy of the oximetry measurement can be improved by using different wavelengths at different saturation ranges. See, for example, U.S. Pat. No. 5,421,329 that describes the use of far red emitters at low saturation levels. An oximeter sensor may utilize either or both of these features by containing new LEDs in addition to LEDs 52 that emit light at different wavelengths than LEDs 52, such as LED 81 shown in FIG. 2. Additional LEDs can similarly be added. If desired, additional wavelengths can be achieved by adding an optical fiber to the sensor assembly. Thus, the oximeter sensor can emit three or more wavelengths of light that are detected by detector 54. The additional LED 81 can be placed in the sensor assembly and driven along with the traditional ones or separately by drive circuit 82 (which is controlled by controller 64) as shown in FIG. 2.

The oximeter (or additional constituent measurement unit) provides the capability to calculate blood constituent values using these additional or alternative wavelengths. The sensor provides the oximeter with additional information the oximeter needs to make these calculations, such as the algorithms needed to calculate blood constituent values for these other wavelengths. The additional information including the algorithms can be stored in memory 56 and read by the oximeter. Sensor memory 56 can also store an indication of the number of wavelengths used in the sensor, the calibration data for properly utilizing the additional LEDs, and can store the wavelength values themselves.

Sensor memory 56 can also store information about when to utilize which LEDs in the sensor. The LEDs can all be utilized all the time, or a subset of the LEDs can be utilized together at a given time. For example, sensor LEDs with different wavelengths (such as LEDs 52 and 81) can be utilized at different times that correspond to different blood oxygen saturation ranges to improve oximetry measurement. The oximeter can read the information in memory 56 to determine when to utilize and to drive particular LEDs. Signal ranges can vary from patient-to-patient. Thus, memory 56 can encode which wavelength or which LEDs should be utilized for a particular patient at particular times to optimize the oximetry measurements.

In another embodiment of the present invention, the time that the sensor is moved or disconnected from the oximeter monitor is written into memory 56. Disconnecting the sensor from the oximeter can be detected from the interruption of the signal to the monitor. The time that the sensor is connected can be saved in memory in the oximeter and recorded into memory 56 when the sensor is subsequently reconnected. Or the oximeter can periodically rerecord a time stamp in memory 56 indicating the current time after predetermined time intervals so that when the sensor is disconnected, the latest time stamp in memory 56 indicates an approximate time that the sensor was disconnected from the oximeter monitor.

Movement in the sensor can be detected by a sensor-off detection, and a subsequent sensor-on detection. Sensor-off and sensor-on conditions can be detected by comparing the signal intensity from detector 54 or a patient's monitored physiological data decoded therefrom with expected ranges encoded in memory. For example, the light intensity received by detector 54 in the IR and red wavelengths falling below or rising above the expected values may be indicative of a sensor-off condition. Further details of methods for determining a sensor-off condition are discussed in Oximeter Sensor with Digital Memory Encoding Sensor Data, U.S. patent application Ser. No. 09/943,805, to Fein et al., filed concurrently herewith (Attorney Docket No. 009103-17910US), which is incorporated by reference herein. Alternately, aggressive movement could be detected by placing a chip in the sensor that detects motion such as MEMS device. A signal from the chip can be interpreted as indicating movement of the sensor. If desired, a combination of aggressive movement with detection of a sensor-off condition can be monitored by the oximeter to determine when the sensor has been moved, and a time stamp can be recorded in memory 56 when movement of the sensor is detected.

In another embodiment of the present invention, the sensor memory 56 stores data indicating that the sensor provides electrical isolation, so that wetness is not a concern. Alternately, sensor memory 56 can store data indicating that electrical isolation isn't provided by the sensor, or a limited amount of electrical isolation is provided. The oximeter can factor in the effects of isolation or non-isolation (determined by reading data in memory 56) when calculating patient physiological data, or when determining variable operating characteristics of the monitor, such as shield grounding for electrical noise minimization or characterization.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. A method for operating an oximeter sensor, the method comprising:

emitting light from a light emitting element;

detecting light from the light emitting element using a light detecting element;

storing digital data in a memory in the sensor, said digital data comprising parameters used to determine the optical transmissivity of a patient, said parameters being related to said light emitting or said light detecting element, keeping tack of changes in a signal from the light detecting element to determine variations in the parameters over time; and recording the changes in the signal in the memory.

2. The method of claim 1 wherein at least one of the parameters corresponds to a brightness of the light emitting element.

3. The method of claim 1 wherein at least one of the parameters corresponds to a sensitivity of the light detecting element.

4. An oximeter system comprising:

an oximeter sensor wherein the sensor comprises:

a light emitting element;

a light detecting element; and a memory for storing digital data, said digital data comprising data used to determine the quality of signals received from the light detecting element, said digital data being related to said light emitting or said light detecting elements; and an oximeter monitor wherein the oximeter monitor computes an optical transmissivity of a patient for wavelengths of the light emitting element using said digital data, and drives the light emitting element with a greater drive current if the patient has a low value for the optical transmissivity to improve the signal to noise ratio of a signal from the light detecting element.

5. The oximeter system of claim 4 wherein the data used to determine the quality of the signals corresponds to a brightness of the light emitting element.

6. The oximeter system of claim 4 wherein the data used to determine the quality of the signals corresponds to a sensitivity of the light detecting element.

7. A method for storing data in an oximeter sensor, the method comprising:

emitting light from a light emitting element;

detecting light from the light emitting element using a light detecting element;

storing digitally encoded data in a memory in the sensor, the digitally encoded data being related to said light emitting or said light detecting element, and being used to determine the accuracy of patient physiological data;

computing an optical transmissivity of a patient for wavelengths of the light emitting element using said digitally encoded data; and driving the light emitting element with a greater drive current if the patient has a low value for the optical transmissivity to improve the signal to noise ratio of a signal from the light detecting element.

8. The method of claim 7 wherein the digitally encoded data corresponds to a brightness of the light emitting element.

9. The method of claim 7 wherein the digitally encoded data corresponds to a sensitivity of the light detecting element.

* * * * *